United States Patent [19]

Tzeghai et al.

[11] Patent Number: 4,755,387
[45] Date of Patent: Jul. 5, 1988

[54] THERAPEUTIC PARTICLES

[75] Inventors: Ghebre E. Tzeghai, Cincinnati; Paul D. Leis, Jr., Hamilton, both of Ohio

[73] Assignee: The Procter & Gamble Company, Cincinnati, Ohio

[21] Appl. No.: 714,606

[22] Filed: Mar. 21, 1985

[51] Int. Cl.[4] .................. A61K 9/42; A61K 9/16
[52] U.S. Cl. .................. 424/450; 424/490; 514/165; 514/866
[58] Field of Search .................. 424/19, 20, 22, 31, 424/38, 450, 490; 514/165, 866

[56] References Cited

U.S. PATENT DOCUMENTS

| | | | |
|---|---|---|---|
| 2,793,979 | 5/1957 | Svedres | 424/22 |
| 2,921,883 | 1/1960 | Reese et al. | 424/19 |
| 3,108,046 | 10/1963 | Harbit | 424/22 |
| 3,119,742 | 1/1964 | Heimlich et al. | 424/19 |
| 3,146,167 | 8/1964 | Lantz, Jr. et al. | 424/22 |
| 3,147,187 | 9/1964 | Playfair | 424/19 |
| 3,965,256 | 6/1976 | Leslie | 424/22 |
| 4,013,784 | 3/1977 | Speiser | 424/19 |
| 4,182,778 | 1/1980 | Hall et al. | 424/72 |
| 4,344,968 | 8/1982 | Aoda et al. | 424/19 |
| 4,483,847 | 11/1984 | Augart | 424/22 |

FOREIGN PATENT DOCUMENTS 1443923  7/1976  United Kingdom .

Primary Examiner—Ronald W. Griffin
Attorney, Agent, or Firm—Richard C. Witte; John V. Gorman; Douglas C. Mohl

[57] ABSTRACT

Therapeutic particles are disclosed which have a coating of a combination of lipids over the therapeutic agent. The lipid coating provides good stomach protection while providing good release of the therapeutic agent in the intestines.

16 Claims, No Drawings

THERAPEUTIC PARTICLES

TECHNICAL FIELD

The prseent invention is related to therapeutic agents which have a coating of a mixture of lipids.

The use of therapeutic agents such as aspirin is widespread as a means for alleviating pain of various types. One problem associated with aspirin for many pople is irritation of the stomach. As a result prior art developments have provided polymeric enteric coatings which allow the aspirin particles to pass through the stomach and into the intestines. The more alkaline environmnt of the intestines dissolves/disrupts the enteric coating allowing the aspirin to be released. Insuring satisfactory coatings (i.e., those that have minimal leakage in the stomach but still release the drug in the intestines) has been a problem continually faced by workers in the field.

Other therapeutic agents are inactivated by the stomach environment (e.g., vitamins, mineral supplements and insulin) and it is desired to have them pass unaltered into the intestines. These agents are also benefited by the present invention.

BACKGROUND ART

There are many references concerning polymeric enteric coatings. U.S. Pat. No. 3,524,910, Aug. 18, 1970 to Holliday et al. disclosed analgesic compositions wherein the analgesic (e.g., aspirin) is coated with ethyl cellulose in a weight amount relative to the amount of analgesic of from 1:22 to 1:50. U.S. Pat. No. 3,656,997, Apr. 18, 1972 to Cordes discloses analgesic containing gelatin capsules having a first coating of an enteric material. U.S. Pat. No. 3,691,090, Sept. 12, 1972 to Kitajima et al. discloses a method of encapsulating aspirin cores with an enteric polymer. U.S. Pat. No. 3,906,086 Sept. 16, 1975 to Guy et al. discloses a particle having an aspirin core and an enteric phthalate coating. U.S. Pat. No. 4,308,251, Dec. 29, 1981 to Dunn et al. discloses aspirin tablets containing aspirin, an enteric material and an erosion promoting agent such as corn starch.

Additional references disclosing coatings on analgesics include U.S. Pat. No. 2,953,497, Sept. 1960 to Press which discloses analgesic granules having a cellulose acetate phthalate coating; U.S. Pat. No. 3,166,476, Jan. 19, 1965 to Lowey which discloses aspirin particles which have a first coating of a material such as gelatin and a second enteric coating; British Pat. No. 1,129,811, Oct. 9, 1968 to Aspro-Nicholas Ltd. which discloses aspirin particles which have a coating of a polysalicylide and possibly a second, unspecified, coating.

Although the use of enteric polymers as disclosed in the above references provide for some stomach protection and release of the drug in the intestines, they are not the final answer. For chronic users of a drug like aspirin minimizing or eliminating stomach damage is a must and this is not achieved by the enteric polymers. The enteric polymers are "pH triggered" and are designed to be distrupted at the pH's found in the intestines, 5-7.5. However, even in the stomach where the pH of the gastric juices is acidic and the enteric should remain intact, most of the stomach muscosal, gastric lining has a higher pH and the enteric coating can be disrupted with stomach irritation the result.

The present invention involves the use of lipids which are not triggerd by pH (acidic or neutral) but are broken down by secretions, from the liver and pancreas, in the intestines. Lipids have been used to coat a variety of drug actives but not in the manner of the present invention.

The use of lipids in many prior references was to provide a sustained release of the drug. U.S. Pat. No. 2,921,883, Jan. 19, 1960 to Reese et al. discloses a mixture of a lipid (e.g., glyceryl tri-dihydroxystearate) and a cellulose derivative to provide a sustained release of the medicament. The pantentees distinguish their release from that given by an enteric coating. U.S. Pat. No. 3,147,187, Sept. 1, 1964 to Playfair discloses a drug mixed with a fat (e.g., glyceryl tristearate), and a swellable gum or proteinaceous material. U.S. Pat. No. 4,483,847, Nov. 20, 1984 to Augart discloses a sustained release composition comprising a mixture of high and low melting point lipids and the active ingredient. The intent of the patente was to achieve sustained release in the gastrointestinal system.

While the prior art discloses a variety of polymric enteric coatings and lipids, the use of lipids to provide an enteric coating of the type of the present invention has not been disclosed. The present inventors have found that a particular lipid coating provides for release in the intestines while minimizing or eliminating release in the stomach.

It is therefore an object of the present invention to provide therapeutic granules which have a more efficient enteric coating.

It is a further object of the present invention to provide theraputic granules which have a coating consisting of a mixture of lipids.

It is still a further object of the present invention to provide a method for treating pain, fever, and inflammation.

These and other objects will become readily apparent from the detailed description which follows. All percentages and ratios herein are by weight unless otherwise specified.

SUMMARY OF THE INVENTION

The present invention to enteric coated theraputic particles wherein the entric coating is a mixture of two lipids (e.g., glyceryl tristearate) and a second lipid (e.g., sorbitan tristearate) wherein the ratio of the former to the latter is from about 1:9 to about 1:1, most preferably 1:4 to about 2:3.

DETAILED DESCRIPTION

The essential as well as optional components of the invention claimed herein are set forth in the paragraphs which follow. In the present application the following terms have the meanings given.

"Pharmaceutically-acceptable" or "pharmacologically-acceptable", as used herein, means that the ingredients used in the compositions are suitable for use in contact with the tissue of humans, without undue toxicity, irritation, allergic response, and the like, commensurate with a reasonable benefit/risk ratio.

The term "comprising", as used herein, means that various other compatible components, including both active and inert ingredients, can be conjointly employed in the composition of this invention. The term "comprising" thus encompasses and includes the more restrictive terms "consisting of" and "consisting essentially of".

By "compatible" herein is meant that the components of the present invention are capable of being commingled without interacting in a manner which would substantially decrease the efficacy of the therapeutic under ordinary use conditions.

THERAPUTIC ACTIVE CORE

The therapeutic actives useful in the present invention may include vitamins, mineral supplements, insulin and preferably nonsteroidals which have analgesic and/or antipyrtic and/or anti-flammatory properties. Aspirin is an example of such a material and is the preferred material. However, there are numrous and other materials which can be used. These include calcium carbaspirin, chloline salicylate, salicylic acid, naproxen, ibuprofen, fenoprofen and mixtures thereof.

The uncoated theraputic particles generally contain about 50% to about 100%, preferably from about 85% to about 95% of the therapeutic active.

Optional components which may be used include diluents, binders, disintegrents, lubricants, glidents, buffering adjuvants and direct acting adjuvants. Numerous pharmaceutically acceptable and compatible materials can be found in various pharmacological references. Two such references are *Pharmaceutical Dosage Forms: Tablets*, Vol. 1, Ed. H. A. Lieberman and L. Lachman, Mercel Dekker, Inc., 1980 and "Proposed Monograph for OTC Internal Analgesic, Antipyretic and Antirheumatic Drugs", Federal Register, July 8, 1977. Both are incorporated herein by reference.

Exemplary material of the above types include dicalcium phosphate and lactose as diluents; gelatin and polyvinylpyrrolidone as binders; corn starch, sodium starch glycolate and cellulosics as disintegrents; stearates as lubricants; fumed silica as glidents; glycine and other amino acids, bicarbonate salts, carbonate salts, magnesium and aluminum hydroxides, aluminum glycinate, citrate salts and borate salts as buffering adjuvants; and caffeine, ascorbic acid and other vitamins, antihistamines and other cough, cold, allergy bronchodilator and antiasthamatic drugs as direct acting adjuvants.

Thes optional components individually may be present at a level of from about 0% to about 50%, preferably from about 5% to about 15% of the uncoated particles.

Lipid Coating

The enteric (the accepted usage of this term means allowing passage through the stomach and into the intestines) coating used with the persent particles is a combination of lipid materials.

The first lipid is selected from the group consisting of glyceryl tristearate, (GTS), commonly referred to as "tristearin", preferably the $\beta'$ form, glyceryl tripalmitate, monopalmityl distearyl triglyceride, dipalmityl monostearyl triglyceride and mixtures thereof. This lipid material is water permable and is important in allowing the active ingredient to be released in the intestines. This lipid generally comprises from about 5% to about 50%, preferably from about 15% to about 45%, most preferably from about 25% to about 40%, of the total lipid coat.

The second lipid is selected from the group consisting of sorbitan tristearate, hexaglycerol hexapalmitate, hexaglycerol hexastearate, decaglycerol decapalmitate, decaglycerol decastearate and mixtures thereof. The preferred material is sorbitan tristearate. This lipid, or mixture, is present at a level of from about 50% to about 95%, preferbly from about 55% to about 85%, most preferbly from about 60% to about 75% of the total lipid coating.

The total lipid coating generally comprises from about 3% to about 45% of the coated particle, preferably from about 10% to about 30%, most preferably from about 15% to about 25%. These levels are far lower than prior art lipid coating levels designed to bypass the stomach.

Optional components which may be used in the lipid coating include a variety of materials. One such material is a conventional polymeric enteric material. Suitable materials include hydroxypropyl methylcellulose phthalate, cellulose acetate phthalate, acrylic anionic polymers (e.g., Eudragit TM -a polymer based on polymethacrylic acid and acrylic acid esters and polyvinyl acetyl phthalate offered by Rohm Pharma).

If present the polymeric enteric comprises from about 5% to about 60% preferably from about 10% to about 25% of the total lipid coating.

Other optional components useful in thee lipid coating include such things as cholesterol and acetylated monoglycerides as plasticizers.

Another execution within the scope of the present invention involves coating the theraputic active with a polymeric enteric material prior to the application of the lipid coating. If used in this manner the polymer material comprises from about 3% to about 20%, preferably from about 5% to about 12% of the total coated particles. This coating may help to release the therapeutic active in the intestines but also provides for a smoother, better surface to apply the lipids.

Optional components useful wth polymeric enterics include surface active agents, particularly nonionic agents, and plasticizers such as triethyl citrate, triacetin, castor oil and acetylated monoglyceride.

The total coated particles of the present invention may be of any size but are preferably in the size range of 0.3 mm to about 3 mm, most preferably from about 0.5 mm to about 1 mm. This preferred range provides for rapid exit of the particles from the stomach.

METHOD OF MANUFACTURE

The present coated particles may be made according to the process outlined in U.S. Pat. No. 4,182,778, Jan. 8, 1980 to Hall et al. incorporated herein by reference. A specific example is set forth below.

Commercially available (Monsanto Chemical Co.) aspirin granules are screened to provide granules with a diameter range of 0.6 to 0.85 mm. Said granules are then coated with the lipid using a Wurster fluidized bed coater (Glatt Air Techniques, Inc., Model WSG5) with a seven inch column diameter.

Two thousand grams of sieved granules are placed in the Wurster coater. The lipid coat components, 265 grams of sorbitan tristearate and 88 grams of glyceryl tristearate are melted and then mixed with a solvent (isopropyl alcohol) at a level of about 40% by weight of the total coating solution and maintained in a liquid state during the coating application via agitation and heat. The coating solution is applied at a rate of 56 ml/min. through a 1.0 mm nozzle and atomized with 53 l/min. air at 45 psig. The bed is fluidized with 115 SCFM air at 39° C. inlet temperature. The exit air temperature under these conditions is about 34° C. The coating operation is continued until all the coating solution is used up.

Alternative processes do not involve the use of the solvent or a different solvent level. If no solvent is used, the temperature of the lipid mixture should be increased to maintain the lipids in liquid form.

FIELD OF USE

The particles of the present invention can be used in tablets, capsules or in any other convenient form. The therapeutic agents are well recognized for treating a wide variety of human ailments. With aspirin and many other nonsteroidals a usual dosage is from about 100 to about 650 mg, preferably from about 200 to about 500 mg.

The following non-limiting examples illustrate the compositions of the present invention.

EXAMPLE I

Aspirin particles about 0.5 mm to 1.0 mm, in diameter were coated with a mixture of sorbitan tristearate, 60%, and glyceryl tristearate, 40%, according to the method described hereinbefoe. The lipid coating amounted to 25% of the total coated particle. When exposed to a 0.1NHC aquous solution as outlined in the Pharmacopeial Forum, pp. 2072-2073 (U.S. Pharmacopeial Convention, Inc.), the particles released none of the coated aspirin.

When in the particles described above, sorbitan tristarate is replaced by hexaglycerol hexapalmitate, hexaglycerol hexastearate, decaglycerol decapalmitate, decaglycerol decastearate and mixtures of these or mixtures with sorbitan tristearate similar results are achieved.

Similarly when glyceryl tristrearate is replaced by glyceryl tripalmitate, monopalmityl distearyl triglyceride, dipalmityl monostearyl triglyceride and mixtures of these or mixtures with glyceryl tristearate similar results are achieved.

EXAMPLE II

Aspirin particles of the same type as those of Example I were first coated with a coating of cellulose acetate phthalate (CAP) plasticized wtih castor oil. This plasticized polymeric coating amounted to 10% of the total coated particle. on top of the CAP coating was applied a coating of a mixture of sorbitan tristearate, 60%, and glyceryl tristearate, 40%. this lipid coating amounted to 15% of the total coated particle.

This particle performed in the same manner as those of Example I.

EXAMPLE III

Particles similar to those of Example I were prepared with the lipid coating amounting to 15% of the total coated particles. The ratio of sorbitan tristearate to glyceryl tristearate was 75:25. These particles performed in the same manner as those of Example I.

EXAMPLE IV

When in Example I aspirin is replaced by insulin, vitamins or mineral supplements, the lipid allows for the therapeutic agent to bypass the stomach and be released in the intestines.

What is claimed is:

1. Thereapeutic active particles comprising a therapeutic active having a lipid coating of a mixture of:
   (a) a lipid selected from the group consisting of glyceryl tristearate, glyceryl tripalmitate, monopalmityl distearyl triglyceride, dipalmityl monostearyl triglyceride and mixtures thereof;
   (b) a lipid selected from the group consisting of sorbitan tristearate, hexaglycerol hexapalmitate, hexaglycerol hexastearate, decaglycerol decapalmitate, decaglycerol decastearate and mixtures thereof,
   wherein the lipid coating comprises from about 3% to about 45% of the coated particle and the ratio of a:b is from about 1:9 to about 1:1.

2. Thereapeutic active particles according to claim 1 wherein the therapeutic active is a nonsteroidal.

3. Therapeutic particles according to claim 2 wherein the lipid coating is from about 10% to about 30% of the coated particle.

4. Therapeutic active particles according to claim 2 wherein the coated particles are from about 0.3 to about 3 mm in diameter.

5. Therapeutic active particles according to claim 2 wherein the a lipid is glyceryl tristearate and the b lipid is sorbitan tristearate.

6. Therapeutic active particles according to claim 5 wherein the ratio of a:b is from about 1:4 to about 2:3.

7. Therapeutic active particles according to claim 6 wherein the therapeutic active is aspirin.

8. Therapeutic active particles according to claim 6 wherein the lipid coating is from about 10% to about 30% of the coated particle.

9. Therapeutic active particles according to claim 2 wherein the therapeutic active has a first coating of a polymeric enteric material and the lipid coating is over the polymeric material.

10. Therapeutic active particles according to claim 9 wherein the polymeric enteric coating is from about 3% to about 20% of the coated particle.

11. Therapeutic active particles according to claim 3 which has a polymeric enteric coating mixed in with the lipid coating.

12. A method of alleviating pain by ingesting particles of claim 1 wherein each particle contains from about 100 to about 650 milligrams of an analgesic active.

13. A method according to claim 12 wherein the particles are according to claim 2.

14. A method according to claim 12 wherein the particles are according to claim 5.

15. A method according to claim 12 wherein the particles are according to claim 7.

16. Therapeutic active granules according to claim 1 wherein the therapeutic active is selected from the group consisting of insulin, vitamins, mineral supplements and mixtures thereof.

* * * * *